(12) United States Patent
Bouhour et al.

(10) Patent No.: US 6,343,231 B1
(45) Date of Patent: Jan. 29, 2002

(54) ACTIVE IMPLANTABLE MEDICAL DEVICE, ESPECIALLY A PACEMAKER, DEFIBRILLATOR AND/OR CARDIOVERTOR OF THE DDD/AAI TYPE WITH EFFORT OPTIMIZED OPERATION

(75) Inventors: Anne Bouhour, Ville-d'Avray; Jean-Luc Bonnett, Montrouge, both of (FR)

(73) Assignee: ELA Medical, S.A., Montrouge (FR)

( * ) Notice: Subject to any disclaimer, the term of this patent is extended or adjusted under 35 U.S.C. 154(b) by 0 days.

(21) Appl. No.: 09/567,413

(22) Filed: May 8, 2000

(30) Foreign Application Priority Data

May 7, 1999 (FR) ............................................. 99 05821

(51) Int. Cl.$^7$ ............................................. A61N 1/368
(52) U.S. Cl. ............................................. 607/9
(58) Field of Search ............................. 607/5, 4, 9, 14, 607/25

(56) References Cited

U.S. PATENT DOCUMENTS

| | | | |
|---|---|---|---|
| 4,945,909 A | 8/1990 | Fearnot et al. | 128/419 |
| 5,318,594 A | 6/1994 | Limousin et al. | 607/9 |
| 5,334,222 A | 8/1994 | Salo et al. | 607/17 |
| 5,873,895 A | 2/1999 | Sholder et al. | 607/9 |

FOREIGN PATENT DOCUMENTS

| | | | |
|---|---|---|---|
| EP | 0 488 904 | 6/1992 | A61N/1/368 |
| EP | 0 600 631 A2 | 6/1994 | A61N/1/368 |

*Primary Examiner*—Scott M. Getzow
(74) *Attorney, Agent, or Firm*—Orrick, Herrington & Sutcliffe LLP

(57) ABSTRACT

An improved active implantable medical device which detects spontaneous atrial and ventricular events, the presence or the absence of an atrio-ventricular spontaneous conduction, and stimulates the atrium and the ventricle, an automatic mode switching operation as between, e.g., DDD and AAI operating modes, for cardiac pacing, which device also includes an activity sensor to discriminate between phases of effort and rest of the patient, and measures the conduction time separating a spontaneous or stimulated atrial event, and a consecutive corresponding spontaneous ventricular event, and provides for a diagnosis of a good or a bad adaptation of the conduction time during the effort phase of the patient. The diagnosis of a good or bad adaptation is performed by an evaluation, during the effort, of the variation of the conduction time in relation to the variation of the heart rate. When the diagnosis indicates a bad adaptation during the effort, the automatic mode switching operation is deactivated and the device is switched to a DDD operating mode such that the atrio-ventricular delay is reprogrammed with a value shorter than the value programmed before, which operating conditions are maintained until the effort is ended.

17 Claims, 2 Drawing Sheets

ACTIVE IMPLANTABLE MEDICAL DEVICE, ESPECIALLY A PACEMAKER, DEFIBRILLATOR AND/OR CARDIOVERTOR OF THE DDD/AAI TYPE WITH EFFORT OPTIMIZED OPERATION

FIELD OF THE INVENTION

The present invention relates to "active implantable medical devices" as such devices are defined by the Council of the European Communities' Jun. 20, 1990, Directive No. 90/385/CEE, more particularly to pacemaker devices, including "multisite" pacing devices (triple or quadruple chamber), defibrillators and/or cardiovertors, which devices are able to deliver to the heart low energy pulses for the treatment of heart rate disorders. The invention also relates more particularly to those active implantable medical devices which include stimulation circuits having an automatic mode switching (AMS) operation, as described, for example, in EP-A-0 488 904 (and its corresponding U.S. Pat. No. 5,318,594) (commonly assigned herewith to ELA Medical, Montrouge, France).

BACKGROUND OF THE INVENTION

Active implantable medical devices are known which include means for providing the stimulation and detection at the same time on the atrium and the ventricle, that can operate in two operating modes, DDD or AAI (the AAI mode being a DDD mode having a lengthened atrio-ventricular delay (AVD)), with automatic switching from one operating mode to the other. The basic operating mode is the AAI mode, with single chamber atrial stimulation. This AAI mode is maintained as long as atrio-ventricular conduction is normal, i.e., as long as each atrial event (detection, corresponding to a spontaneous activity, or stimulation) is followed by an associated ventricular detection.

In certain circumstances, in particular during episodes of effort (i.e., when the patient is active and not at rest), atrio-ventricular blocks (AVB), known as "paroxystic blocks", involving a depolarization defect of the ventricle, can appear. In such a case, the pacemaker switches into an automatic DDD operating mode, with parameters optimized for a temporary AVB situation. Preferably, to favor a return of spontaneous atrio-ventricular conduction, the pacemaker applies a relatively long atrio-ventricular delay in order to allow for a spontaneous atrio-ventricular (AV) conduction of the patient to occur before a ventricular stimulation is delivered.

After the disappearance of the AVB, and thus after a reestablishment of spontaneous AV conduction, the pacemaker automatically returns to the AAI operating mode, since a certain number of corresponding conditions have been fulfilled, as described in the aforementioned patent.

Thus, the control algorithm for the automatic mode switching (herein the "DDD ASM" algorithm), in order to favor the occurrence of spontaneous conduction, uses a rather long conduction delay value (also known as the atrio-ventricular delay or "AVD") before switching to deliver a ventricular stimulation. The time between the atrial event and the consecutive ventricular detection is known as the "conduction interval" or "conduction time", namely, the "PR conduction interval" for the time between an atrial detection and a corresponding consecutive ventricular detection, and the "AR conduction interval" for the time between an atrial stimulation and a corresponding consecutive ventricular detection.

Indeed, it is desirable to let a spontaneous AV conduction occur, and generally preferable from a physiological point of view (better filling of the cardiac cavities, etc.), in comparison to a stimulated operation.

SUMMARY OF THE INVENTION

The starting point of the present invention is the observation by the applicants that, in certain cases, it is not always desirable to try to let the spontaneous AV conduction of the patient occur. Indeed, there are certain types of AVB for which the AV conduction defects of certain patients can result in an absence of the reduction (and even a lengthening of same) of the PR (or AR) conduction time during a patient effort. Such a conduction exists, but it is not hemodynamically good, and it would therefore be preferable instead to stimulate the ventricle.

The present invention, therefore, proposes an improved method and device making it possible to diagnose whether the adaptation of the conduction time during a patient effort is a good adaptation or a bad adaptation, i.e., beneficial or not beneficial to the patient, and to cure bad adaptation situations by suitable modifications of the pacemaker operating parameter(s). The type of device to which the invention applies is a DDD ASM type device, as described, for example, in EP-A-0 488 904 and U.S. Pat. No. 5,318,594 mentioned above. Such a device includes means for sensing atrial and ventricular spontaneous events, means for detecting the presence or the absence of an atrio-ventricular spontaneous conduction and means for delivering ventricular and atrial stimulation, the ventricular stimulation being applied in the absence of a detection of a spontaneous atrio-ventricular conduction, after the completion of a programmed atrio-ventricular delay started on a spontaneous or stimulated atrial event. Such means are well known in the art and any suitable circuit, logic devices and software may be used.

According to the present invention, this device further includes functionality and/or means to discriminate between phases of effort and rest of the patient bearing the device, means for measuring an atrio-ventricular conduction time separating a spontaneous or stimulated atrial event and a corresponding consecutive spontaneous ventricular event, and a means for diagnosing a good or a bad adaptation of conduction time during the patient effort. The diagnosing means operates by evaluation, during the phase of patient effort, of the conduction time variation in relation to any heart rate variation.

Very advantageously, the device of the present invention responds to a diagnosis of a bad adaptation of the conduction interval during an effort, by deactivating the automatic mode switching of the device, and switching the device to operate in a DDD mode and reprogramming the atrio-ventricular delay with a value that is shorter than the value previously programmed.

Preferably, discriminating between phases of effort and rest of the patient is achieved by use of an activity sensor which responds to the patient's level of effort.

In one embodiment, the diagnosis means is activated only if, during the phases of evaluation, the atrial events are either all spontaneous events or all stimulated events. Further, the diagnosis means preferably determines that there is a bad adaptation during an effort when the aforementioned evaluation reveals an absence of a reduction of the conduction time when there is an increase in the heart rate.

The above-mentioned evaluation is preferably operated by memorizing successive determined values of the conduction time, or by memorizing averages of the successive determined values. The values are measured for a plurality of successive predetermined heart rate values, and the values of the measured conduction time are possibly retained for evaluation only when they are included within a predefined range around the corresponding predetermined heart rate.

In one embodiment, the diagnosis means is activated if the increase in the heart rate from the beginning of the phase of effort is greater than a predetermined threshold. Further, in yet another embodiment, there is provided means for limiting the value of the atrio-ventricular delay in the phase of effort when the heart rate becomes greater than a predetermined threshold.

In yet another embodiment, the diagnosis means determines that there is a bad adaptation during the effort when, for a predetermined number of cardiac cycles presenting a frequency greater than a predetermined heart rate, the conduction time is greater than a predetermined maximum duration.

Preferably, the de-activation of the automatic mode switching, the switching into DDD operating mode, and the reprogramming of the atrio-ventricular delay are operated throughout the duration of the phase of effort, with the former mode of operation being restored only after return of the patient's activity to a rest phase.

BRIEF DESCRIPTION OF THE DRAWINGS

Further features, characteristics, and advantages of the present invention will become apparent to a person of ordinary skill in the art in view of the following detailed discussion of a preferred embodiment of the invention, which is described with reference to the attached drawings in which.

DETAILED DESCRIPTION OF THE INVENTION

Figure 1:
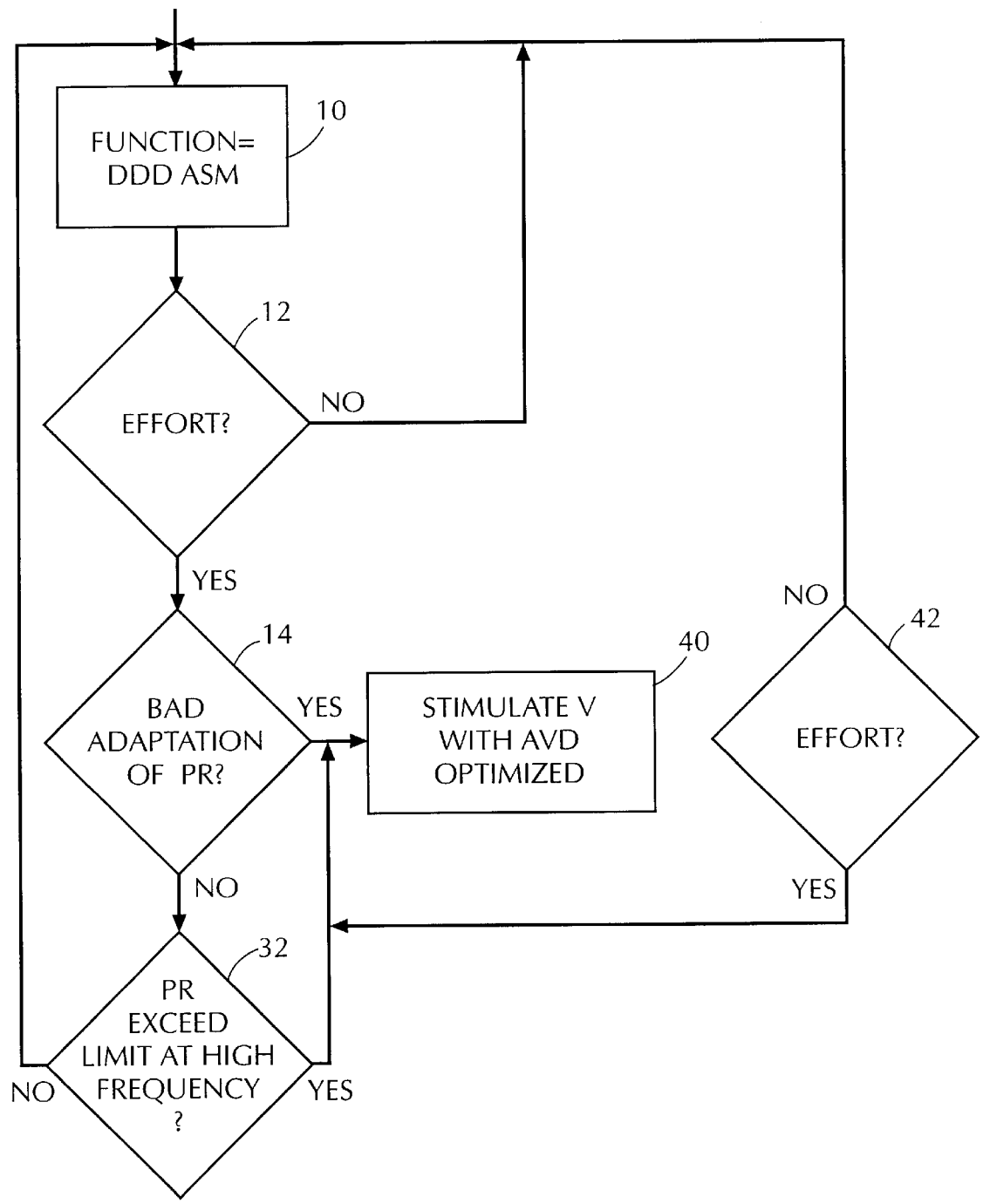
FIG. 1 is a flow chart of a control algorithm for implementing the various functions of the invention.

The present invention is advantageously implemented as a DDD AMS control algorithm which is implemented in software that is loaded into a traditional type of pacemaker. The CHORUS brand of dual chamber pacemakers available from ELA Médical are suitable devices, which may be configured with the software implementing the functions of the present invention at the time of manufacture or thereafter by downloading software by telemetry into an already implanted device.

Initially, the pacemaker, which detected a paroxystic AVB, operates in an AAI mode under DDD AMS operation (stage 10). The functions activated by the software of the present invention, as preferably implemented, are set only during the phases of effort of the patient. Such phases are detected (stage 12) by an activity sensor, making it possible to detect quickly a change of activity of the patient bearing the device. The activity sensor is typically an accelerometer ("sensor G"), as taught, for example, in EP-A-0 550 293) and its counterpart U.S. Pat. No. 5,330,510 (ELA Médical) or EP-A-0 750 920 (and its counterpart U.S. Pat. No. 5,249,572) (ELA Médical). The latter references describe a pacemaker with dual sensors, one being a physiological parameter sensor (minute volume) and one being an activity parameter sensor (acceleration), and a system that combines these two sensors in determining when there is an effort (e.g., non rest activity) of these two sensors. Thus, other activity sensors and combinations thereof also could be used.

The first stage of the functions concerns diagnosing a bad adaptation of the PR (or AR) conduction time during a phase of patient effort. For this purpose, the way in which the conduction time varies in relation to the increase in the heart rate is evaluated (stage 14). This diagnosis is made at the beginning of an effort, and it is operated only if the atrial activity is stable throughout the diagnosis, i.e., if the atrial events are all spontaneous or are all stimulated. In such a case, the device permanently memorizes an average PR (or AR) conduction time, for example, for four successive frequency bands, the bands being separated by, for example, 10 bpm. For simplicity, only PR intervals are illustrated in the drawings.

The analysis of this data is carried out in the following way, which way of course is not intended to be restrictive of the manner in which the data may be analyzed. For each multiple of 10 bpm of the value of the heart rate between 50 and 120 bpm, one defines a range of intervals [e.g., 60000/f−20 ms; 60000/f+20 ms] corresponding to frequency f. Thus, for example, for f=60 bpm, the interval range is 980 ms to 1,020 ms, and for f=100 bpm, the interval range is 580 ms to 620 ms.

On each atrial event (detected or stimulated), if the conduction interval that finishes in the absence of a perturbing element (i.e., an atrial or ventricular extrasystolie, noise) and belongs to an interval range such as defined above, the device then memorizes the PR (or AR) conduction time counted starting from this atrial event, dependent on the corresponding frequency. Thus, typically up to four values of conduction time per frequency interval value are memorized.

Figure 2:
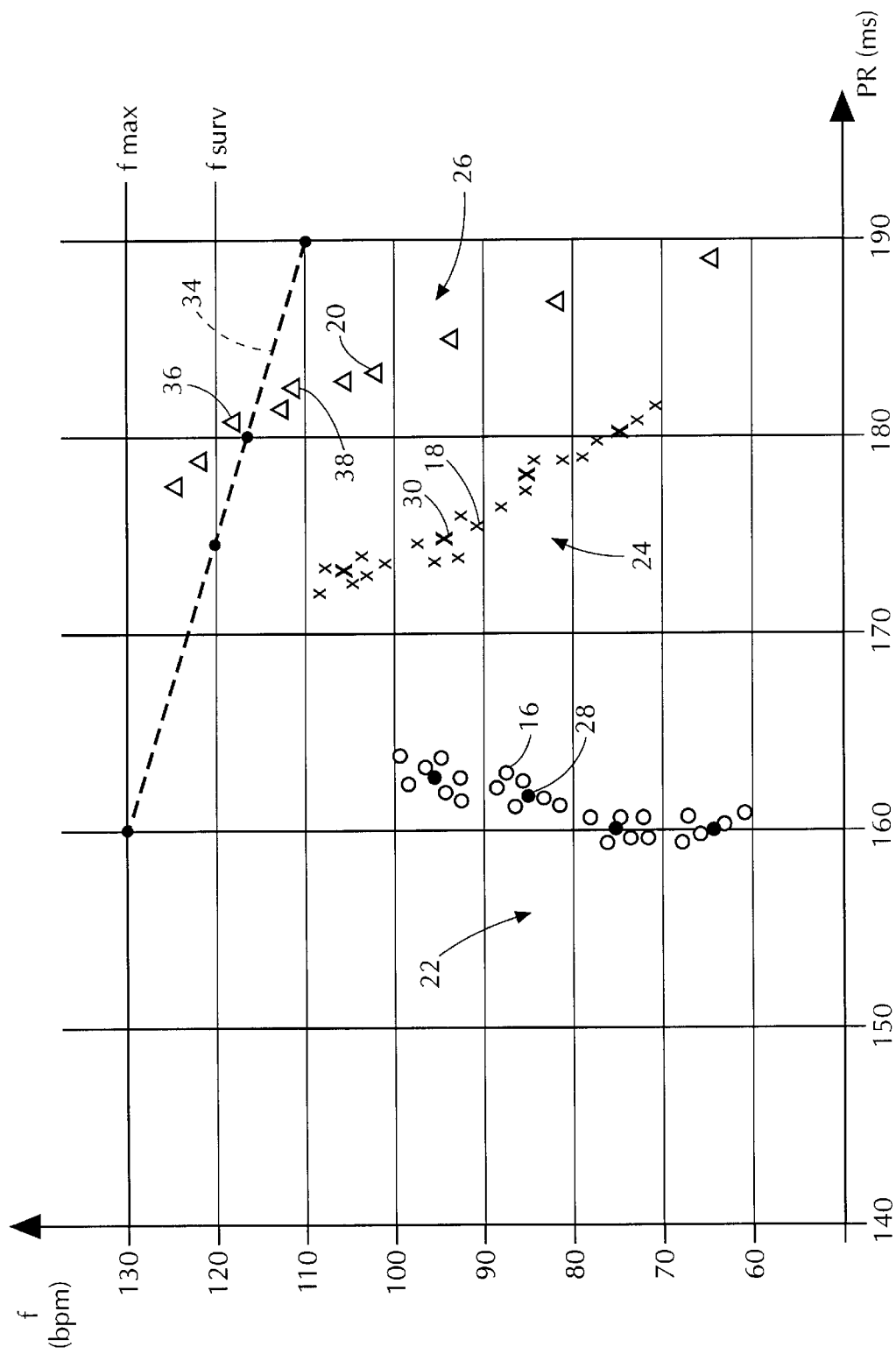
FIG. 2 illustrates the variations of the conduction time in relation to the heart rate for various situations of good or bad adaptation of the conduction time during the effort.

These values are plotted on FIG. 2, and correspond to a series of points such as 16, 18, 20. In the three cases illustrated, they demonstrate a difference in the conduction time during the effort (respectively, series 22, 24 and 26).

One thus obtains conduction time values that one can average over several measures, for example, four measures, as located on 28 or 30 on FIG. 2, respectively for the series of items 22 and 24.

The values thus obtained for a given frequency f reached during the effort will be indicated PRavef. The diagnosis is then made when one collects a sufficient number of PRavef values, for example, the PRavef values for four successive frequencies separated by 10 bpm. Alternatively, one also can test the reduction in the PR (or AR) conduction time compared to a minimal threshold, for example, a reduction in the conduction time of at least 4 ms for an increase in frequency of 10 bpm.

Starting from the collected data which is classified by heart rate intervals, the device determines if the PR (or AR) conduction time adaptation with the effort is good or bad.

One can thus consider that the adaptation is good when the conduction time decreases each time when the frequency increases—more precisely, each time the frequency increases by 10 bpm, i.e:

$$PRave_{fd} > PRave_{fd+10} > PRave_{fd+20} > PRave_{fd+30},$$

wherein fd corresponds to the first value of the frequency multiple with bpm increments, reached at the beginning of the effort. Also, an hysteresis factor (not shown) can be associated with each of these values.

The diagnosis is made once for every phase of effort, when an increase in the frequency of at least 30 bpm is realized. This makes it possible to conclude that there is a good or a bad adaptation of PR during the effort.

If the effort was too low, for example, when an increase in the heart rate is less than 30 bpm, or if one could not memorize PR (or AR) values for each of the plurality of frequency bands separated by 10 bpm, or if the stimulated/detected state of the atrial activity had changed (i.e., switching between detected and stimulated atrial events during the effort phase), then it is considered that the diagnosis of conduction time adaptation during the effort is impossible (i.e., unreliable) for this phase of effort, and one will await the next phase of effort to commence a new diagnosis.

In addition or in the alternative to the foregoing, a bad conduction time adaptation during the effort may be detected by examining the maximum value of the atrio-ventricular delay (AVD) at a high cardiac frequency (stage 32). In this regard, if the current heart rate becomes high, for example, exceeds the programmed maximum frequency fmax less 20 bpm, thus giving the value designated as fsurv (frequency of monitoring) on FIG. 2, one considers that, if the adaptation during the effort is good, the AVD should not exceed a given value. The given value may be fixed either in an absolute value (typically 180 ms), or expressed as a percentage of the duration of the cardiac cycle (typically a 35% limit, located at 34 on FIG. 2). One thus examines during successive cycles if the conduction time exceeds (as in 36) or does not exceed (as in 38) the limit thus fixed.

If, for example, this limit is exceeded on four successive cycles, this means that the PR (or AR) conduction time is longer than the maximum value envisaged, and the device thus determines the existence of a bad adaptation during the effort.

When a bad adaptation during the effort is diagnosed by one and/or the other of the methods described above, the action taken by the device is (stage 40) to deactivate the automatic mode switching algorithm DDD AMS, so that the device will not seek to return to the AAI operating mode during the duration of the effort, and to maintain the pacemaker in an ordinary DDD operating mode (without AMS), and to reprogram the AVD with a shorter value, optimized for permanent stimulation during the effort phase.

The search for spontaneous conduction (thus implying the application of a longer AVD) will be undertaken only when the effort is finished, i.e., when the activity sensor indicates a return to a rest state (stage 42).

One skilled in the art will appreciate that the present invention can be practiced by other embodiments than those described above and by the use of numerical parameters other than those provided above, which described embodiments are presented for purposes of illustration and not of limitation.

We claim:

1. An active implantable medical device having a DDD operating mode and an AAI operating mode and an automatic mode switching operation including:
    means for detecting spontaneous atrial and ventricular events including anatrio-ventricular conduction;
    means for determining a heart rate from the detected events;
    means for providing a programmed atrio-ventricular delay in response to one of an atrial stimulation and a detected spontaneous atrial event; and
    means for ventricular and atrial stimulation, said ventricular stimulation being applied in response to an absence of a detection of an atrio-ventricular conduction following said provided programmed atrio-ventricular delay, wherein the improvement comprises:
    means for discriminating between a phase of effort and a phase of rest;
    means for measuring an atrio-ventricular conduction time separating an atrial event from a consecutive corresponding spontaneous ventricular event, wherein the atrial event is one of a spontaneous and a stimulated event; and
    means for diagnosing one of a good adaptation and a bad adaptation of the conduction time during the determined effort, including means for evaluating a conduction time variation in relation to a variation of the heart rate during said effort.

2. The device of claim 1, further comprising:
    means, responsive to a diagnosis of a bad adaptation during the effort, for deactivating the automatic mode switching operation of the device.

3. The device of claim 1, further comprising:
    means, responsive to a diagnosis of a bad adaptation during the effort, for switching the device to a DDD operating mode.

4. The device of claim 1, further comprising:
    means, responsive to a diagnosis of a bad adaptation during the effort, for reprogramming the atrio-ventricular delay to have a value shorter than the provided programmed value.

5. The device of claim 1, further comprising:
    means, responsive to a diagnosis of a bad adaptation during the effort, for deactivating the automatic mode switching operation of the device, for switching the device to a DDD operating mode, and for reprogramming the atrio-ventricular delay to have a value shorter than the provided programmed value.

6. The device of claim 1, wherein the means for discriminating between said effort and rest phases comprises an activity sensor.

7. The device of claim 1, further comprising means for determining whether the atrial events detected during a phase of effort are all spontaneous events or all stimulated events, wherein the means for diagnosis is responsive to said determining means determining that said atrial events are all spontaneous events or all stimulated events.

8. The device of claim 1, further comprising means for determining an increase in the heart rate, and means for determining an absence of a reduction of the conduction time during an increase in the heart rate, wherein the diagnosing means determines that there is a bad adaptation during the effort in response to a determined absence of a reduction of the conduction time during an increase in the heart rate.

9. The device of claim 8, wherein the diagnosing means further comprises means for memorizing successive values of the conduction time recorded for a plurality of predetermined successive heart rate values.

10. The device of claim 9, in which the values of the conduction time measured are retained for evaluation only when they are included inside a preset interval around the corresponding predetermined heart rate.

11. The device of claim 9, wherein the diagnosing means further comprises means for averaging successive values of the conduction time recorded for a plurality of predetermined successive heart rate values and memorizing said average value.

12. The device of claim 11, in which the averaged value of the conduction time measured is retained for evaluation only when it is included inside a preset interval around the corresponding predetermined heart rate.

13. The device of claim 1, further comprising means for determining an increase in the heart rate and comparing said increase to a predetermined threshold, and means for activating the diagnosing means if the increase in the heart rate since the beginning of the phase of effort is higher than said predetermined threshold.

14. The device of claim 1, further comprising means for comparing said heart rate to a predetermined threshold, and means for limiting the value of the atrio-ventricular delay in a phase of effort in response to the heart rate becoming higher than said predetermined threshold.

15. The device of claim 1, wherein the diagnosing means determines that there is a bad adaptation during the effort when, for a predetermined number of cardiac cycles presenting a heart rate greater than a predetermined heart rate, the conduction time is longer than a predetermined maximum duration.

16. The device of claim 15, further comprising means for determining an increase in the heart rate, and means for determining an absence of a reduction of the conduction time during an increase in the heart rate, wherein the diagnosing means determines that there is a bad adaptation during the effort in response to a determined absence of a reduction of the conduction time during an increase in the heart rate and said conduction time being longer than a predetermined maximum duration for said predetermined number of cardiac cycles.

17. The device of claim 1, further comprising means, responsive to a diagnosis of a bad adaptation during an effort, for deactivating the automatic mode switching operation and switching the device to a DDD operating mode and reprogramming the atrio-ventricular delay to a value shorter than the provided programmed value during said phase of effort; and means for restoring the device to an automatic mode switching operation in response to a return to a phase of rest following said phase of effort.

* * * * *